United States Patent
Mendiratta et al.

(10) Patent No.: US 8,021,862 B2
(45) Date of Patent: Sep. 20, 2011

(54) PROCESS FOR PREPARING HUMAN G-CSF (75) Inventors: Sanjeev Kumar Mendiratta, Gujarat (IN); Vibhor Saraswat, Gujarat (IN); Pankaj R. Patel, Gujarat (IN)

(73) Assignee: Cadilla Healthcare Limited, Ahmedabad (IN)

( * ) Notice: Subject to any disclaimer, the term of this patent is extended or adjusted under 35 U.S.C. 154(b) by 0 days.

(21) Appl. No.: 12/280,496

(22) PCT Filed: Mar. 5, 2007

(86) PCT No.: PCT/IN2007/000105
§ 371 (c)(1),
(2), (4) Date: Dec. 4, 2008

(87) PCT Pub. No.: WO2007/102174
PCT Pub. Date: Sep. 13, 2007

(65) Prior Publication Data
US 2009/0305354 A1    Dec. 10, 2009

(30) Foreign Application Priority Data

Mar. 6, 2006  (IN) ........................... 309/MUM/2006

(51) Int. Cl.
C12P 21/02    (2006.01)
A61K 45/00   (2006.01)
A61K 38/19   (2006.01)

(52) U.S. Cl. .................... 435/71.1; 435/71.3; 435/69.5; 536/23.5; 424/85.1

(58) Field of Classification Search .................. None
See application file for complete search history.

(56) References Cited

FOREIGN PATENT DOCUMENTS
EP        0 459 630 A    12/1991

OTHER PUBLICATIONS

Yim S C et al: "High-level secretory production of human granulocyte-colony stimulating factor by fed-batch culture of recombinant *Escherichia coli*" Bioprocess and Biosystems Engineering, vol. 24, No. 4, Nov. 2001, pp. 249-254, XP002449223 ISSN: 1615-7591 cited in the application the whole document p. 250, left-hand col., line 13-right-hand col., line 21.

Jevsevar S et al: "Production of nonclassical inclusion bodies from which correctly folded protein can be extracted" Biotechnology Progress, vol. 21, No. 2, Mar. 2005, pp. 632-639, XP002426305 ISSN: 8756-7938 cited in the application the whole document.

Choi Seung-Jin et al: "Plasmid stability in long-term hG-CSF production using L-arabinose promoter system of *Escherichia coli*" Journal of Microbiology and Biotechnology, vol. 10, No. 3, Jun. 2000, pp. 321-326, XP008083145 ISSN: 1017-7825 cited in the application.

Fatemi Seyed Safa-Ali et al: "Selection of a suitable strain from recombinant *Escherichia coli* strains with the same genetic structure expressing periplasmic hGM-CSF." Journal of Bioscience and Bioengineering, vol. 96, No. 6, Dec. 2003, pp. 578-580, XP002449225 ISSN: 1389-1723 the whole document.

Jeong Ki Jun et al: "Secretory production of human granulocyte colony-stimulating factor in *Escherichia coli*" Protein Expression and Purification, vol. 23, No. 2, 2001, pp. 311-318, XP002263043 ISSN: 1046-5928 cited in the application the whole document.

*Primary Examiner* — Bridget E Bunner
*Assistant Examiner* — Fozia Hamud
(74) *Attorney, Agent, or Firm* — Ladas & Parry LLP (57) ABSTRACT

The present invention discloses an improved process for the production of G-CSF in high yield via a high salt-induced increase in plasmid stability during the production phase.

12 Claims, 6 Drawing Sheets

PROCESS FOR PREPARING HUMAN G-CSF

FIELD OF INVENTION

The present invention relates to an improved process for the production of G-CSF in high yield via a high salt-induced increase in plasmid stability during the production phase.

BACKGROUND OF THE INVENTION

The cytokine Granulocyte Colony Stimulating Factor (G-CSF) treatment significantly improves the quality of life among patients with severe chronic neutropenia [Jones et al. JAMA 270: 1132-1133 (1993)]. The G-CSF is a potent endogenous trigger for the release of neutrophils from bone marrow stores and for their activation for enhanced antimicrobial activity. G-CSF has been widely evaluated in various preclinical models of acute illness, with generally promising results [Marshall J. C. Shock 24: 120-9 (2005)]. Due to its proven efficacy during chemotherapy cycles, the G-CSF is an important biopharmaceutical drug used in oncology. G-CSF has been cloned and expressed in various types of cells, e.g. microbial cells [Souza L. M. Science 232: 61-65 (1986); Hu Z. Y. et al. Zhongguo Shenghua Yaowu Zazhi (1999), 20: 55-57], yeast cells [Lasnik M. A. et al. Biotechnol. Bioeng. 81: 768-774 (2003); Lee S. M. et al. Korean patent KR 160934 B1 19981116], rice cells [Hong et al. Protein Expr Purif. Epub ahead of print (2005)], feline cells [Yamamoto et al. Gene 274: 263-269 (2001)], Chinese Hamster Ovary cells [Monaco L. et al. Gene. 180:145-150 (1996)], insect cells [Shinkai et al. Protein Expr Purif. 10: 379-385 (1997)], and even in transgenic goat [Ko J. H. et al. Transgenic Res. 9: 215-22 (2000)]. For pharmaceutical use the G-CSF is produced primarily in Escherichia coli [Jevsevar S. et al. Biotechnol. Prog. 21: 632-639 (2005)], where it is produced as inclusion bodies, which are insoluble aggregates of the recombinant protein in non-native conformation [Baneyx F. & Mujacic M. Nature Biotechnol. 22: 1399-1408 (2004)], that generally do not have biological activity [Bernardez C. E. Curr. Opin. Biotechnol. 9: 157-163 (1998)]. The technologies of its secretory production [Jeong K. J. & Lee S. Y. Protein Expr Purif 23: 311-318 (2001); Lee S. Y. et al. Methods Mol. Biol. 308: 31-42 (2005)], have also been reported. Secretory expression generally results into the release of properly folded form of G-CSF into the periplasmic space or extracellular medium, but the yields are much lesser than those obtained with inclusion bodies. It is therefore commercially beneficial to express G-CSF in E. coli as inclusion bodies. Properly folded, biologically active G-CSF protein is easily obtained from inclusion bodies in a commercially viable manner, using denaturation and renaturation processes applied subsequent to the isolation and solubilization of inclusion bodies [Rudolph R, In Protein Engineering: Principles and Practice; Cleland, J. L., Craik, S. C., Eds.; Wiley-Liss, Inc.: New York, 1996; pp 283-298; Rathore A. S. et al. J Pharm Biomed Anal. 32:1199-1211 (2003)].

One of the most efficient methods of recombinant protein production in E. coli is fed-batch, which can be carried out, in cyclic and non-cyclic modes. The non-cyclic processes are less complex and therefore more suitable for industrial production. In fact, prior art describes one of the highest GCSF yields from a non-cyclic fed-batch process which is in the range of 4.2-4.4 g/L [Yim S C et al. Bioprocess and Biosystems Engineering (2001), 24, 249-254]. Carrying out fed-batch fermentation in cyclic mode in order to obtain higher cumulative yield results in high plasmid instability [Choi S.-J. et al. J. Microbiol. Biotechnol. 10: 321-326 (2000)], thereby limiting the robustness of the process.

In general, in order to have high expression of the product it is imperative to keep the product gene-containing extrachromosomal plasmid inside the cell in its proper form. This is generally achieved by maintaining selection pressure on the recombinant microorganism by adding a suitable antibiotic to the culture broth. Increase in expression level of G-CSF by adding antibiotic (Ampicillin) every 1-2 h during fermentation to decrease the 'segregational nonstability' of recombinant strain has been reported (Krivopalova G. N. et al. Russian Patent RU 2158303 C2 20001027). The regulatory requirement of the evidence of antibiotic clearance from the final product necessitates the limit of its use. Higher usage of antibiotics may also have a higher potential of having an undesirable environmental impact. But the decrease in antibiotic selection pressure often results in decreased plasmid stability and expression levels, which compromises the robustness of process. Therefore, it is a technical challenge to limit the use of antibiotic while increasing the plasmid stability and expression level of the product, especially during production phase. Further, low plasmid stability during production phase can also be due to metabolic stress [Saraswat V. et al. FEMS Microbiol. Lett. 179: 367-373 (1999)], and might lead to low expression levels [Cheng C. et al Biotechnol. Bioeng. 56: 23-31 (1997)], typically in high volume cultures.

Besides maintaining high antibiotic selection pressure, plasmid stability can be improved at the level of vector construction [Schweder T. et al. Appl Microbiol Biotechnol. 38:91-93 (1992); Pan S. H. and Malcom B. A. Biotechniques. 29:1234-1238 (2000)]. In process it can be improved by adjusting the culture conditions, such as avoiding nutrient starvation [Smith & Bidochka Can. J. Microhiol. 44: 351-355 (1998)]. While carrying out large-scale substrate-limiting fed-batch processes, nutrient limitation/starvation is imminent, and adding antibiotic either too frequently or in large amounts are also impractical and expensive solutions to maintain high product yield and high plasmid stability in a process of low complexity. Therefore, there is a clear need to develop an alternate process for preparing G-CSF in high volumetric yields by maintaining high plasmid stability using a simple and robust process.

SUMMARY OF INVENTION

The present invention describes a non-cyclic fed-batch process to produce Granulocyte Colony Stimulating Factor (G-CSF) in high volumetric yields in Escherichia coli by maintaining high plasmid stability in the culture, with the use of Potassium in combination with either Magnesium or Sodium ions in high concentrations in the production medium and culture broth.

DESCRIPTION OF THE INVENTION

The present invention relates to an improved fermentation process for the production of Granulocyte Colony Stimulating Factor (G-CSF) at improved levels of volumetric yield. It also discloses culturing conditions for improved plasmid stability that further leads to a high volumetric yield of G-CSF. The process of the invention involves a non-cyclic fed-batch process via multiple inductions, carried out in the presence of high concentration of Potassium, in combination with other inorganic salts such as Sodium, Magnesium and the like, at high concentrations in the production media. Surprisingly, when such a process using the salts of the of the present invention as is hereinafter described in details, was used in combination with high specific growth rate, it still maintained high plasmid stability leading to further increase of volumetric yield.

The present invention is further described in detail below:

Any Granulocyte Colony Stimulating Factor (also referred here as 'G-CSF') polypeptide can be utilized. The term "Granulocyte Colony Stimulating Factor" or "G-CSF" refers to native G-CSF, muteins, fragments, fusions, analogs and derivatives thereof either exhibiting at least 60% biological or receptor binding activity as the native hG-CSF or retaining at least about 80% amino acid identity. Examples of such G-CSF sequence includes Genbank Sequence ID GI:27437048 and those described in U.S. Pat. No. 4,810,643.

Escherichia coli cells are transformed with suitable expression vector comprising the coding sequence of G-CSF and a suitable promoter selected from t7, tac, and similar promoters along with other vector components using transformation techniques well known in art.

In the process described below the fermentation refers to an aerobic growth of microorganisms, preferably recombinant E. coli, for the production of G-CSF. In such a process, the batch phase of growth refers to the period in which after inoculation, no nutrient, except ammonium hydroxide is added (if needed) to the culture broth in the fermenter. The culture broth is a suspension of cells, media, and derivatives of the media and cells (if any). The substrate limiting fed-batch in growth phase refers to that part of growth phase in which major increase in biomass (at least 2 doublings) takes place by adding the fed batch growth media to the culture broth in such a way that the concentration of the main carbon/energy source (for example, glucose) is limiting. The flow rate of the said media determines the specific growth rate of the culture. Pre-induction media refers to the media, having a different composition than the growth media, which is added to the culture broth before adding the inducer (for example IPTG). Induction is the process of appreciably increasing the concentration of the G-CSF in the cells, as determined by tools known in the prior art, by addition of inducer (for example, IPTG and lactose). Production media has a different composition than the growth media and is added to the culture broth in the fermenter during the induction of the G-CSF gene. The production media was also added in such a way that the concentration of substrate (for example, glucose) remains limiting. The flow rate of production media determines the specific growth rate of the culture during production phase.

The host cells of E. coli, previously transformed with a suitable expression vector encoding G-CSF, were initially cultured at 37° C. in shaker-flasks to develop the seed for fermenter. The seed culture was used for inoculating the sterile growth media in a fermenter. The substrate-limiting fed-batch mode of growth phase of fermentation is initiated once the recombinant E. coli culture starts to grow and the glucose concentration in the culture broth drops down to 0.5 g/L or less. The feed of fed-batch growth medium, added in substrate-limiting fed-batch manner, is kept continuous (exponential or constant rate) or discontinuous during growth phase. After achieving a cell density of 1-60 g/L dry cell weight and a glucose concentration less than 0.5 g/L in the culture broth, addition of the pre-production medium is done and subsequently the feed of production media started and continued in a continuous- or discontinuous-substrate-limiting fashion. Multiple inductions of G-CSF gene are made with IPTG. The average specific growth rate is not decreased during or after the additions of the inducer. The pH is maintained at about 5-7. The temperature is maintained at about 30-42° C. After 2 to 48 h of adding pre-production medium, the culture medium is removed and subjected to down stream processing according to the techniques described in art.

The media of the growth phase comprise carbon and energy sources selected from the group comprising of glucose, glycerol, etc. and the like or mixtures thereof, complex media components selected from the group comprising of yeast extract, tryptone, peptone, casein enzyme hydrolysate, soyabean casein hydrolysate and the like, or mixtures thereof, suitable salts/nutrients selected from the group comprising of citric acid, potassium chloride, sodium chloride, magnesium sulphate, di-ammonium hydrogen phosphate, potassium dihydrogen phosphate, sodium butyrate, thiamine, glycine, and zinc chloride.

Other fermentation conditions like aeration, agitation, inoculum, time of inoculation etc. are all chosen as per convenience as are known in prior art.

The pre-production medium comprises, complex media components selected from yeast extract, tryptone, peptone, casein enzyme hydrolysate, soyabean casein hydrolysate, along with nutrients such as thiamine, glycine and the like or mixtures thereof; antibiotics like kanamycin, and ampicillin and the like. Suitable salts are selected from the group comprising of citric acid, potassium chloride, sodium chloride, magnesium sulphate, di-ammonium hydrogen phosphate, potassium dihydrogen phosphate, sodium butyrate, and zinc chloride such that the medium contains high level of K ion concentration in combination with either Na or Mg ions.

The production medium contains a carbon source in addition to the constituents of the pre-production medium. Suitable carbon source can be selected from the group consisting of glycerol, glucose, fructose and the like or mixtures thereof. The preferred carbon source of the present invention is glucose. During production phase, the culture broth is maintained with high level of K ions in combination with either Na or Mg ions. The concentration of K ions is maintained at about 60 mM to about 300 mM, Na ions at about 60 mM to about 300 mM, and Mg ions at about 150 mM to about 250 mM in the culture broth. In a preferred embodiment, the K ion concentration is 90 mM to 150 mM, Na ion concentration is 60 mM to 120 mM, and the Mg ion concentration in the culture broth is in the range of 180 mM to 220 mM.

In a further embodiment, the addition of thiamine in high concentration (in the range of 5 g/L to 10 g/L) provides yield of G-CSF in the range of 5-6 g/L.

The process of the present invention results in the production of G-CSF in high yields (5-9.5 g/L) with maintenance of high plasmid stability throughout the growth and the production phase (75-90%).

Example 1

Effect of High Concentrations of Na and K Ions on Plasmid Stability and Volumetric Yield The experiment was carried out in a 30-L fermenter. A seed culture of *E. coli* BL21 (DE3) cells transformed with the human G-CSF gene was inoculated in the growth media of the following composition.

| Component | Concentration before inoculation |
| --- | --- |
| $KH_2PO_4$ | 13.3 g/L |
| $(NH_4)_2HPO_4$ | 4.0 g/L |
| Yeast extract | 1.0 g/L |
| Glucose | 10.0 g/L |
| Citric acid | 1.7 g/L |
| $MgSO_4 \cdot 7H_2O$ | 1.2 g/L |
| Trace element solution | 20.0 mL/L |
| Kanamycin | 50 mg/L |

Trace metal solution:

| Component | Concentration |
| --- | --- |
| $FeCl_3 \cdot 6H_2O$ | 0.162 g/L |
| $ZnCl_2 \cdot 4H_2O$ | 0.0144 g/L |
| $CoCl_2 \cdot 6H_2O$ | 0.12 g/L |
| $Na_2MoO_4 \cdot 2H_2O$ | 0.012 g/L |
| $CaCl_2 \cdot 2H_2O$ | 0.006 g/L |
| $CuCl_2$ | 1.9 g/L |
| $H_3BO_3$ | 0.5 g/L |

Adding the following 'fed-batch growth media' in substrate limiting fed-batch mode brought about the major increase in biomass:

| Component | Concentration |
| --- | --- |
| Glucose | 700 g/L |
| $MgSO_4 \cdot 7H_2O$ | 20 g/L |
| Trace element solution | 20 mL/L |
| Kanamycin | 500 mg/L |

In growth phase ammonium hydroxide was used as the pH regulator to maintain the pH in the range of 6.8 to 7.0. The temperature was maintained at 37° C. After achieving optical density of about 50 AU (at 600 nm) in Batch 2 the pre-induction media, consisting of the following composition, was added in the culture broth:

| Component | Concentration |
| --- | --- |
| Yeast extract | 84.38 g/L |
| Potassium chloride | 75.41 g/L |
| Sodium chloride | 123.13 g/L |
| Thiamine hydrochloride | 8.44 g/L |

The final concentration of Potassium and Sodium cations in the culture broth was about 120 mM and 250 mM, respectively.

The feeding of the following production media was subsequently started:

| Component | Concentration |
| --- | --- |
| Glucose | 270 g/L |
| $MgSO_4 \cdot 7H_2O$ | 1 g/L |
| Yeast extract | 214 g/L |
| Thiamine hydrochloride | 7 g/L |
| Potassium chloride | 8.94 g/L (only in Batch 2) |
| Sodium chloride | 17.5 g/L (only in Batch 2) |

The expression of G-CSF gene was induced by multiple additions of filter-sterilized solution of IPTG to the culture broth. In production phase ammonium hydroxide was used as the pH regulator to maintain the pH 6.8. The temperature was maintained at 37° C. Kanamycin was added to the culture to put selection pressure. The amount of Kanamycin used during production phase of Batch 2 (37.5 mg, added once), was about 1% of the amount used in Batch 1 (2925 mg, multiple additions) in order to greatly challenge the effect of salts on plasmid stability.

Figure 1:
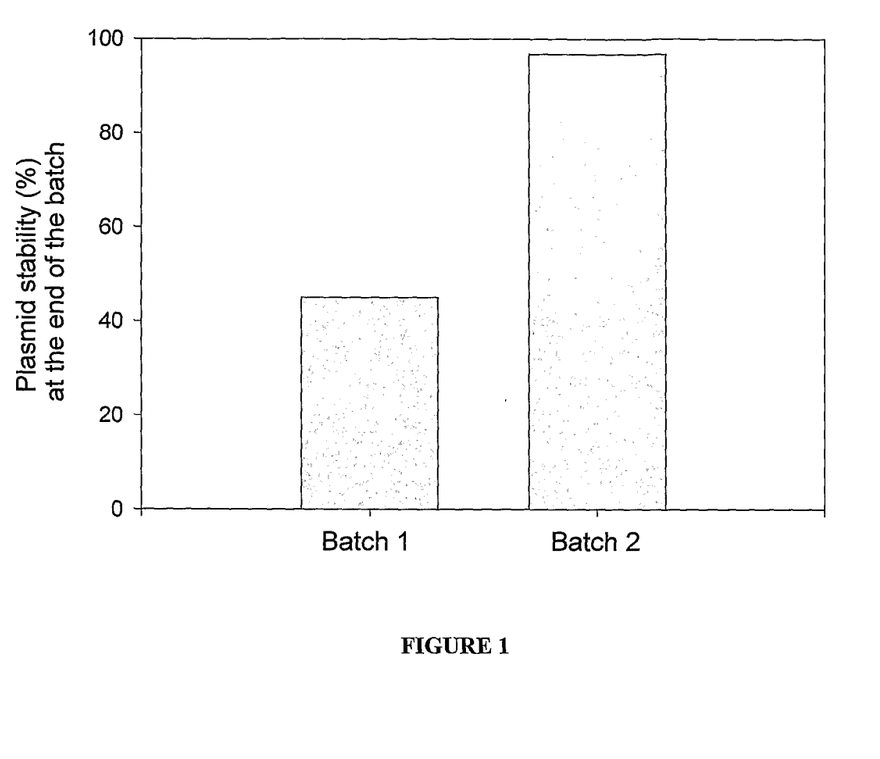
FIG. 1 shows the effect of using high concentration of Potassium and Sodium cations in production phase on the stability of G-CSF gene-containing plasmid in BL21(DE3) cells at the time of batch harvest. Batch 2 was carried out with high concentrations of Potassium and Sodium salts, whereas Batch 1 was carried out without high concentrations of Potassium and Sodium salts in production phase. The batches were carried out separately in a 30-L fermenter.

The plasmid stability was determined by first aseptically collecting the end-of-the-batch sample in a sterile tube and aseptically spreading appropriate volume of the suitable diluted sample on Luria-Bertani medium with and without Kanamycin (50 mg/L). The plates were incubated at 37° C. for 48 hours and the plates, having statistically significant colonies were counted. A value obtained by dividing the number of colonies obtained on Kanamycin-containing plates with those on Kanamycin non-containing plates was used to calculate plasmid stability. The plasmid stability in Batch 2 (96.8%) was more than twice, as compared to the plasmid stability in Batch 1 (45.0%), thereby showing the importance of Sodium and Potassium cations in improving the plasmid stability (FIG. 1).

Figure 2:
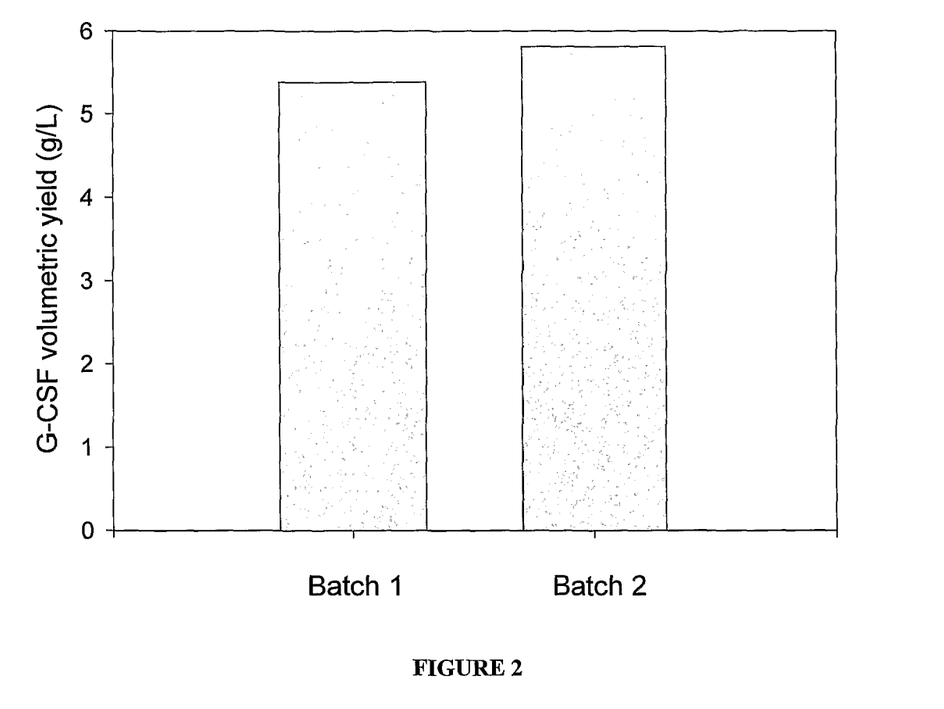
FIG. 2 shows the effect of using high concentration of Potassium and Sodium cations in production phase on G-CSF volumetric yield in harvested batches. Batch 2 was carried out with high concentrations of Potassium and Sodium salts, whereas Batch 1 was carried out without high concentrations of Potassium and Sodium salts in production phase. The batches were carried out separately in a 30-L fermenter.

The volumetric yield of G-CSF, as determined by densitometric quantification of the GCSF band with respect to the standard plot of authentic standard, after SDS-PAGE, was 5.38 g/L in Batch 1 and 5.81 g/L in Batch 2. The volumetric yield in Batch 2 was about 8% higher than that of Batch 1 (FIG. 2).

Example 2

Effect of High Concentrations of Magnesium and Potassium Cations on Plasmid Stability and Volumetric Yield The experiment was carried out in a 30-L fermenter. Since the production phase media of both batches (Batch 3 and Batch 4) were identical including the concentration of Potassium cation, except only the concentration of Magnesium cation, the results reflected the effect of the combination of Potassium and Magnesium cation. A seed culture of *E. coli* BL21 (DE3) cells transformed with the human G-CSF gene was inoculated in the growth media of the following composition.

| Component | Concentration before inoculation |
|---|---|
| KH$_2$PO$_4$ | 13.3 g/L |
| (NH$_4$)$_2$HPO$_4$ | 4.0 g/L |
| Yeast extract | 1.0 g/L |
| Glucose | 10.0 g/L |
| Citric acid | 1.7 g/L |
| MgSO$_4$•7H$_2$O | 1.2 g/L |
| Trace element solution | 20.0 mL/L |
| Kanamycin | 50 mg/L |

Trace metal solution:

| Component | Concentration |
|---|---|
| FeCl$_3$•6H$_2$O | 0.162 g/L |
| ZnCl$_2$•4H$_2$O | 0.0144 g/L |
| CoCl$_2$•6H$_2$O | 0.12 g/L |
| Na$_2$MoO$_4$•2H$_2$O | 0.012 g/L |
| CaCl$_2$•2H$_2$O | 0.006 g/L |
| CuCl$_2$ | 1.9 g/L |
| H$_3$BO$_3$ | 0.5 g/L |

Adding the following 'fed-batch growth media' in substrate limiting fed-batch mode brought about the major increase in biomass:

| Component | Concentration |
|---|---|
| Glucose | 700 g/L |
| MgSO$_4$•7H$_2$O | 20 g/L |
| Trace element solution | 20 mL/L |
| Kanamycin | 500 mg/L |

In growth phase ammonium hydroxide was used as the pH regulator to maintain the pH in the range of 6.8 to 7.0. The temperature was maintained at 37° C. After achieving optical density of about 50 AU (at 600 nm) the pre-induction media, consisting of the following composition, was added in the culture broth:

| Component | Concentration |
|---|---|
| Yeast extract | 84.38 g/L |
| Potassium chloride | 75.44 g/L |
| Thiamine hydrochloride | 8.38 g/L |
| Magnesium Sulfate | 187.06 g/L (only in Batch 4) |

The feeding of the production following media was subsequently started:

| Component | Concentration |
|---|---|
| Glucose | 270 g/L |
| Magnesium Sulfate | 1 g/L (only in Batch 3) |

-continued

| Component | Concentration |
|---|---|
| Magnesium Sulfate | 50.3 g/L (only in Batch 4) |
| Yeast extract | 214 g/L |
| Thiamine hydrochloride | 7 g/L |
| Potassium chloride | 8.94 g/L |

The expression of G-CSF gene was induced by multiple additions of filter-sterilized solution of IPTG to the culture broth. In production phase ammonium hydroxide was used as the pH regulator to maintain the pH 6.8. The temperature was maintained at 37° C. Kanamycin was added to the culture to put selection pressure. The equal amount of Kanamycin (37.5 mg, added once) was used during production phase. The concentration of Potassium and Magnesium cations in the culture broth during production phase was about 120 mM and 200 mM, respectively.

Figure 3:
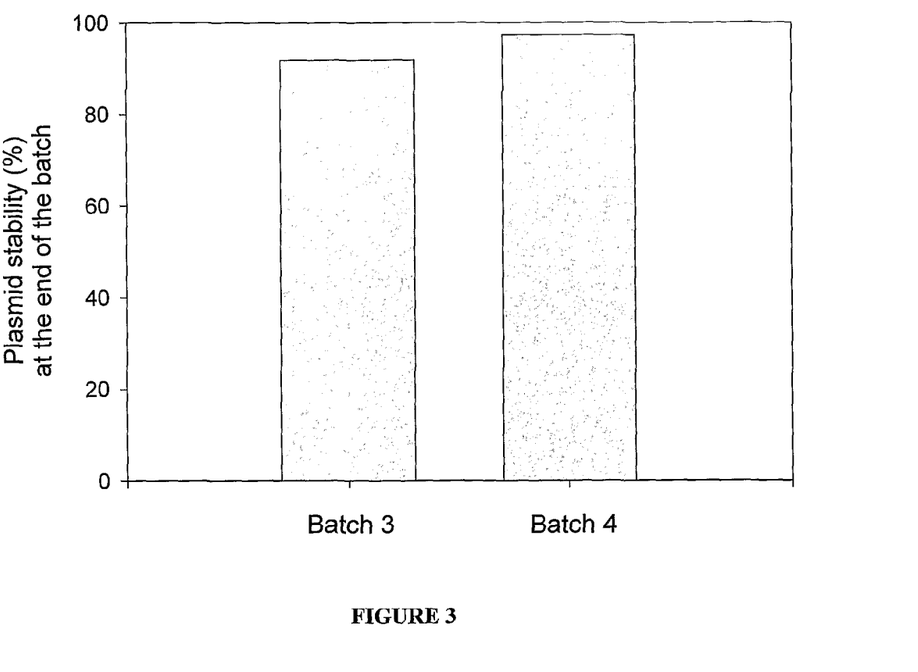
FIG. 3 shows the effect of using high concentration of Magnesium and Potassium cations in production phase on the stability of G-CSF gene-containing plasmid in BL21 (DE3) cells at the time of batch harvest. Batch 4 was carried out with high concentration Magnesium salt, whereas in Batch 3 high concentration of Magnesium salt was not used in production phase. Both batches were carried out with high concentration of Potassium salt, separately in a 30-L fermenter.

The plasmid stability was determined as described previously The plasmid stability in Batch 4 (97.3%) was about 6% higher than the plasmid stability in Batch 3 (91.8%), thereby showing the effectiveness of Magnesium and Potassium cations in improving the plasmid stability (FIG. 3). The plasmid stability obtained in presence of Magnesium and Potassium cations was 116.2% higher than that in Batch 1 (without high concentration of salts in production phase).

Figure 4:
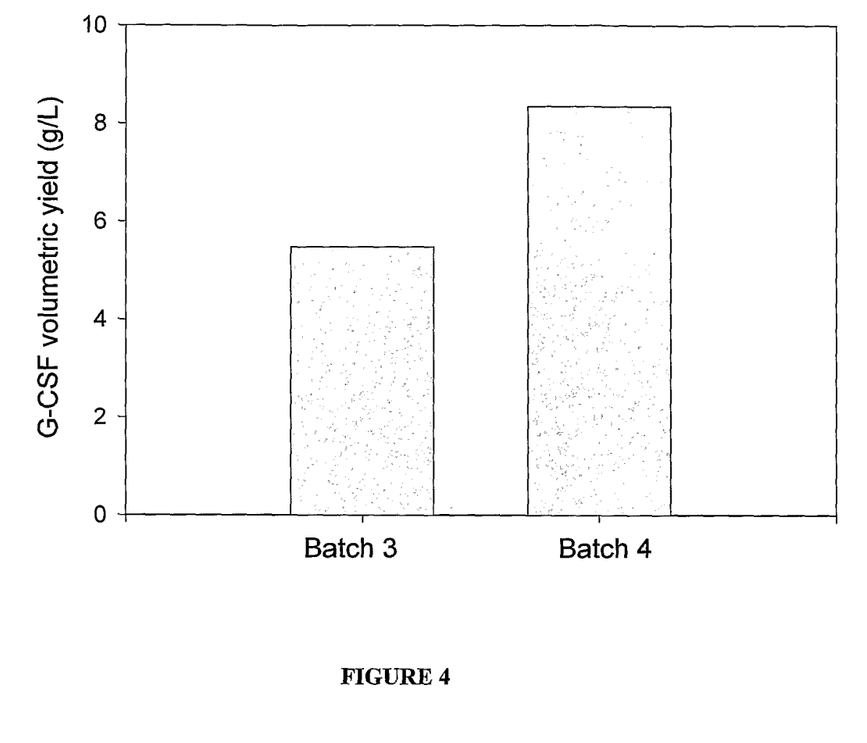
FIG. 4 shows the effect of using high concentration of Magnesium and Potassium cations on G-CSF volumetric yield in harvested batches. Batch 4 was carried out with high concentration Magnesium salt, whereas in Batch 3 high concentration of Magnesium salt was not used in production phase. Both batches were carried out with high concentration of Potassium salt separately in a 30-L fermenter.

The volumetric yield of G-CSF, as determined by densitometric quantification of the GCSF band with respect to the standard plot of authentic standard, after SDS-PAGE, was 5.48 g/L in Batch 3 and 8.35 g/L in Batch 4 (FIG. 4). The volumetric yield in Batch 4 was about 55% higher than that on Batch 1.

Example 3

Effect of High Specific Growth Rate During Production Phase on Volumetric Yield

The experiment was carried out in a 30-L fermenter. The production phase media composition of both batches (Batch 4 and Batch 5) were identical including the concentrations of Potassium and Magnesium cations. The average specific growth rate during production phase of Batch 5 was higher than that in production phase of Batch 4. A seed culture of *E. coli* BL21 (DE3) cells transformed with the human G-CSF gene was inoculated in the growth media of the following composition.

| Component | Concentration before inoculation |
|---|---|
| KH$_2$PO$_4$ | 13.3 g/L |
| (NH$_4$)$_2$HPO$_4$ | 4.0 g/L |
| Yeast extract | 1.0 g/L |
| Glucose | 10.0 g/L |
| Citric acid | 1.7 g/L |
| MgSO$_4$•7H$_2$O | 1.2 g/L |
| Trace element solution | 20.0 mL/L |
| Kanamycin | 50 mg/L |

Trace metal solution:

| Component | Concentration |
|---|---|
| FeCl$_3$•6H$_2$O | 0.162 g/L |
| ZnCl$_2$•4H$_2$O | 0.0144 g/L |
| CoCl$_2$•6H$_2$O | 0.12 g/L |

-continued

| Component | Concentration |
|---|---|
| $Na_2MoO_4 \cdot 2H_2O$ | 0.012 g/L |
| $CaCl_2 \cdot 2H_2O$ | 0.006 g/L |
| $CuCl_2$ | 1.9 g/L |
| $H_3BO_3$ | 0.5 g/L |

Adding the following 'fed-batch growth media' in substrate limiting fed-batch mode brought about the major increase in biomass:

| Component | Concentration |
|---|---|
| Glucose | 700 g/L |
| $MgSO_4 \cdot 7H_2O$ | 20 g/L |
| Trace element solution | 20 mL/L |
| Kanamycin | 500 mg/L |

In growth phase ammonium hydroxide was used as the pH regulator to maintain the pH in the range of 6.8 to 7.0. The temperature was maintained at 37° C. After achieving optical density of about 50 AU (at 600 nm) the pre-induction media, consisting of the following composition, was added in the culture broth:

| Component | Concentration |
|---|---|
| Yeast extract | 84.38 g/L |
| Potassium chloride | 75.44 g/L |
| Thiamine hydrochloride | 8.38 g/L |
| Magnesium Sulfate | 187.06 g/L |

The feeding of the following production media was subsequently started:

| Component | Concentration |
|---|---|
| Glucose | 270 g/L |
| Magnesium Sulfate | 50.3 g/L |
| Yeast extract | 214 g/L |
| Thiamine hydrochloride | 7 g/L |
| Potassium chloride | 8.94 g/L |

The expression of G-CSF gene was induced by multiple additions of filter-sterilized solution of IPTG to the culture broth. In production phase ammonium hydroxide was used as the pH regulator to maintain the pH 6.8. The temperature was maintained at 37° C. Kanamycin was added to the culture to put selection pressure. Equal amount of Kanamycin (37.5 mg, added once) was used during production phase. The average specific growth rate during production phase in Batch 4 was about 0.04 l/h, whereas that in Batch 5 was about 0.07 l/h.

Figure 5:
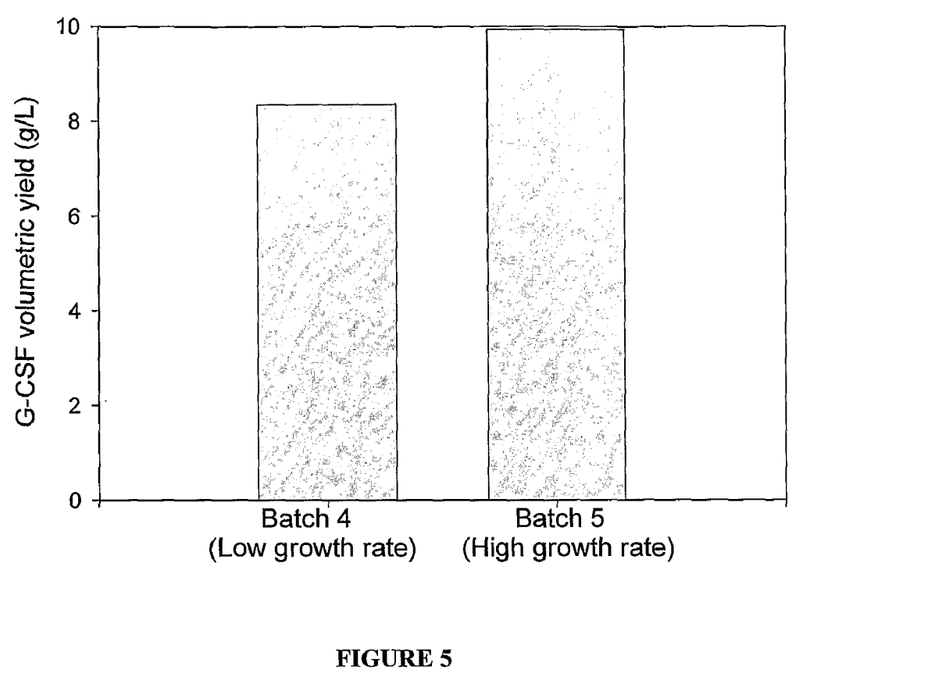
FIG. 5 shows the effect of using high specific growth rate in production phase on G-CSF volumetric yield in harvested batches. During production phase Batch 4 had average specific growth rate of about 0.04 l/h, whereas Batch 5 had average specific growth rate of about 0.07 l/h. Both batches were carried out with high concentrations of Potassium and Magnesium salts, separately in a 30-L fermenter.

The volumetric yield of G-CSF determined, as described previously, to be 8.35 g/L in Batch 4 and 9.94 g/L in Batch 5. The volumetric yield in Batch 5 was about 19% higher than that on Batch 4 (FIG. 5). The plasmid stability in the end-of-the-batch samples of both batches was high (>75%).

Example 4

Effect of Using High Concentration of Thiamine in Production Phase on Volumetric Yield The experiment was carried out in a 30-L fermenter. A seed culture of *E. coli* BL21 (DE3) cells transformed with the human G-CSF gene was inoculated in the growth media of the following composition.

| Component | Concentration before inoculation |
|---|---|
| $KH_2PO_4$ | 13.3 g/L |
| $(NH_4)_2HPO_4$ | 4.0 g/L |
| Yeast extract | 1.0 g/L |
| Glucose | 10.0 g/L |
| Citric acid | 1.7 g/L |
| $MgSO_4 \cdot 7H_2O$ | 1.2 g/L |
| Trace element solution | 20.0 mL/L |
| Kanamycin | 50 mg/L (In Batch 1) |
| Ampicillin | 100 mg/L (In Batch 6) |

Trace metal solution:

| Component | Concentration |
|---|---|
| $FeCl_3 \cdot 6H_2O$ | 0.162 g/L |
| $ZnCl_2 \cdot 4H_2O$ | 0.0144 g/L |
| $CoCl_2 \cdot 6H_2O$ | 0.12 g/L |
| $Na_2MoO_4 \cdot 2H_2O$ | 0.012 g/L |
| $CaCl_2 \cdot 2H_2O$ | 0.006 g/L |
| $CuCl_2$ | 1.9 g/L |
| $H_3BO_3$ | 0.5 g/L |

Adding the following 'fed-batch growth media' in substrate limiting fed-batch mode brought about the major increase in biomass:

| Component | Concentration |
|---|---|
| Glucose | 700 g/L |
| $MgSO_4 \cdot 7H_2O$ | 20 g/L |
| Trace element solution | 20 mL/L |
| Kanamycin | 500 mg/L (In Batch 1) |
| Ampicillin | 50 mg/L of culture broth at each addition only in Batch 6. Total six additions were made during 'fed batch growth' phase of the batch. |

In growth phase ammonium hydroxide was used as the pH regulator to maintain the pH about 6.8. The temperature was maintained at 37° C. After achieving optical density of about 50 AU (at 600 nm) the feeding of the following production media was started:

| Component | Concentration |
|---|---|
| Glucose | 270 g/L |
| $MgSO_4 \cdot 7H_2O$ | 1 g/L |
| Yeast extract | 214 g/L |
| Thiamine hydrochloride | 7 g/L (Only in Batch 1) |
| Kanamycin | 2.925 g (added multiple times in Batch 1) |
| Ampicillin | 2.689 g (added multiple times in Batch 6) |

The expression of G-CSF gene was induced by multiple additions of filter-sterilized solution of IPTG to the culture broth. In production phase ammonium hydroxide was used as the pH regulator to maintain the pH 6.8. The temperature was maintained at 37° C.

Figure 6:
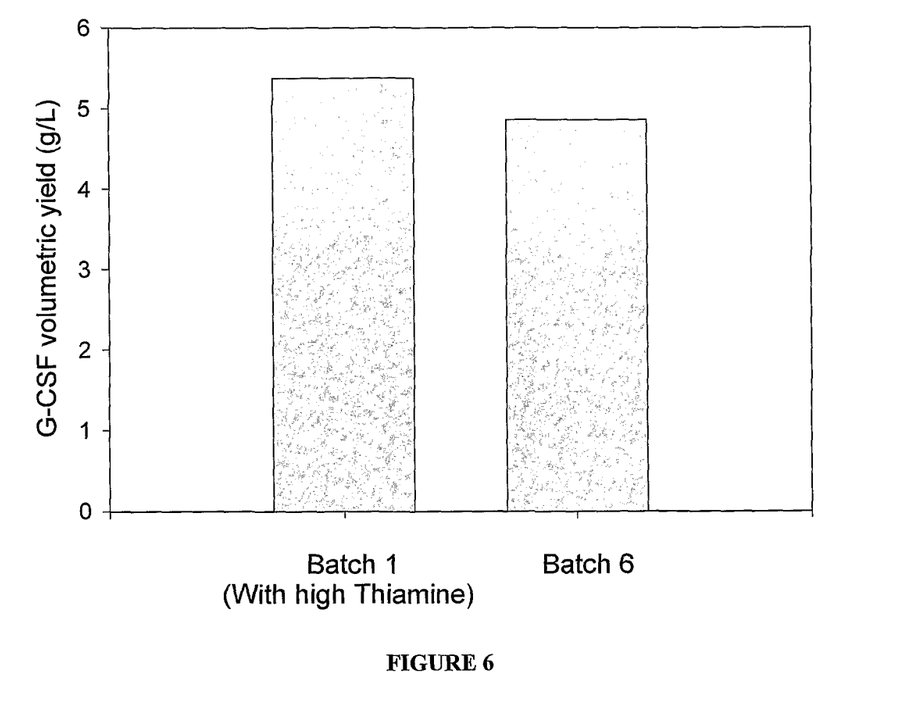
FIG. 6 shows the effect of using high concentration of thiamine in production phase on G-CSF volumetric yield in harvested batches. During production phase Batch 1 had 7 g/L thiamine in the production medium, whereas Batch 6 was done without using any thiamine in the production medium. Both batches were carried out separately in a 30-L fermenter.

The volumetric yield of G-CSF was determined, as described previously. The volumetric yield in end-of-batch sample of Batch 1 (high thiamine batch) was about 10.7% higher than that of in Batch 6 (4.86 g/L), thereby showing the effectiveness of high concentration of thiamine in improving the G-CSF volumetric yield (FIG. 6).

Advantages of the Process:
(1) Higher volumetric yield allows the larger yield at a smaller scale, thereby limiting the capital expenditure on scale-up.
(2) High volumetric yield is achieved using media components (Magnesium, Potassium, and Magnesium salts) of very low cost.
(3) A culture having high plasmid stability is more capable of producing volumetric yield of G-CSF in metabolic stressful conditions, such as G-CSF gene expression in condition of high specific growth rate.

We claim:

1. An improved process for obtaining high volumetric yields of Granulocyte Colony Stimulating Factor (G-CSF) comprising i) inoculating a fermenter with a suitable recombinant *E. coli* culture transformed with an expression vector comprising a nucleic acid sequence that encodes G-CSF and ii) culturing the recombinant *E. coli* through pre-production and production phase of fermentation to express the nucleic acid sequence encoding G-CSF in a culture broth wherein the culture broth comprises potassium (K) ions in a concentration range of 60 mM to 180 mM in combination with inorganic cations selected from sodium (Na) in a concentration range of 90 mM to 300 mM, and magnesium (Mg) in a concentration range of 150 mM to 250 mM.

2. The process as claimed in claim 1, wherein the culture broth comprises a complex medium component selected from the group consisting of yeast extract, tryptone, peptone, casein enzyme hydrolysate, and soybean casein hydrolysate.

3. The process as claimed in claim 1, wherein the process is a substrate limiting fed batch process.

4. The process as claimed in claim 1, wherein multiple inductions of the nucleic acid sequence encoding G-CSF are carried out during the production phase.

5. The process as claimed in claim 1, wherein the culture broth further comprises one or more carbon sources selected from the group consisting of glucose, glycerol, and fructose.

6. The process as claimed in claim 1, wherein an average specific growth rate is maintained to be the same between the production and the pre-production phases.

7. The process as claimed in claim 1, wherein the concentration of the K ions is 90 mM to 150 mM, Na ions is 60 mM to 120 mM, and Mg ions is 180 mM to 220 mM.

8. The process as claimed in claim 1, wherein the recombinant *E. coli* express at least 75% plasmid stability of G-CSF.

9. A process of improving plasmid stability of Granulocyte Colony Stimulating Factor (G-CSF) expressed in recombinant *E. coli* comprising i) inoculating a fermenter with a suitable recombinant *E. coli* culture transformed with an expression vector comprising a nucleic acid sequence that encodes G-CSF and ii) culturing of recombinant *E. coli* through pre-production and production phase of fermentation to express the nucleic acid sequence encoding G-CSF in a culture broth wherein the culture broth comprises potassium (K) ions in the concentration range of 60 mM to 180 mM in combination with inorganic cations selected from sodium (Na) in a concentration range of 90 mM to 300 mM, and magnesium (Mg) in a concentration range of 150 mM to 250 mM.

10. The process as claimed in claim 1, wherein the culture broth further comprises an antibiotic wherein the concentration of antibiotic in production phase is lower than that used in growth phase.

11. A process for producing G-CSF comprising the steps of
i) inoculating a fermenter with an *E. coli* culture in a culture broth, wherein the *E. coli* culture is transformed with an expression vector comprising a nucleic acid sequence that encodes G-CSF;
ii) increasing the biomass of the *E. coli* culture, by batch and fed batch mode;
iii) adding pre-induction medium to the culture broth; and
iv) adding production medium to the culture broth in a substrate limiting fed batch mode in which multiple inductions of the nucleic acid sequence encoding G-CSF are carried out so as to produce G-CSF;
wherein the production medium has a final concentration of potassium (K) from 60 mM to 180 mM, a final concentration of sodium (Na) from 90 mM to 300 mM, and a final concentration of magnesium (Mg) from 150 mM to 250 mM.

12. The process as claimed in claim 1, wherein the volumetric yields of G-CSF is in the range of 5 g/L to 9.5 g/L.

* * * * *